United States Patent [19]

Singh

[11] Patent Number: 5,175,152

[45] Date of Patent: Dec. 29, 1992

[54] COMPOSITION CONTAINING EPHEDRINE BASE AND ALKYL SALICYLATE FOR THE DELIVERY OF EPHEDRINE BASE IN VAPOR FORM

[76] Inventor: Nikhilesh N. Singh, 5299 Spring Grove Ave., Cincinnati, Ohio 45217-1087

[21] Appl. No.: 590,646

[22] Filed: Sep. 28, 1990

[51] Int. Cl.⁵ ............................................. A61K 31/615
[52] U.S. Cl. ............................................. 514/162
[58] Field of Search ................................... 514/162

[56] References Cited

U.S. PATENT DOCUMENTS

| | | | |
|---|---|---|---|
| 2,196,322 | 4/1940 | Nitardy et al. | 167/58 |
| 2,785,103 | 3/1957 | Tabern et al. | |
| 2,868,691 | 1/1959 | Porush et al. | |
| 3,138,526 | 6/1964 | Mattia et al. | 167/55 |
| 3,236,729 | 2/1966 | Dick | 167/58 |
| 3,467,754 | 9/1969 | Mercer et al. | 424/253 |
| 3,639,622 | 2/1972 | Greengard et al. | 424/308 |
| 4,292,301 | 9/1981 | Keith et al. | 424/28 |
| 4,486,436 | 12/1984 | Sunshine et al. | 424/253 |
| 4,522,826 | 6/1985 | Sunshine et al. | 514/569 |
| 4,778,673 | 10/1988 | Vernizzi et al. | 424/10 |
| 4,839,354 | 6/1989 | Sunshine et al. | 514/226.5 |

FOREIGN PATENT DOCUMENTS

| | | |
|---|---|---|
| 520987 | 3/1982 | Austria . |
| 0072462 | 2/1983 | European Pat. Off. . |
| 2613225 | 10/1988 | France . |
| 99927 | 9/1973 | German Democratic Rep. . |

OTHER PUBLICATIONS

Drug Development & Industrial Pharmacy, 14,119 (1988), Bhalla, H. L. and Toddywala.
Journal of Pharmacy & Pharmacology, 24, Suppl., 65 (1972), Beckett, A. H. Gorrod, J. W. and Taylor, D. C.

Primary Examiner—S. J. Friedman
Attorney, Agent, or Firm—Daniel F. Nesbitt; Gary M. Sutter; Ronald L. Hemingway

[57] ABSTRACT

A method of delivering ephedrine base in vapor form from a composition containing the ephedrine base and an alkyl salicylate. Methyl salicylate is the preferred alkyl salicylate. Optional ingredients in the composition include aromatic compounds such as menthol, camphor, and various other essential oils. The method is particularly useful in the treatment of nasal congestion and bronchial asthma. A preferred means of delivering the ephedrine base in vapor form in the treatment of nasal congestion and bronchial asthma is a vapor inhaler.

21 Claims, No Drawings

COMPOSITION CONTAINING EPHEDRINE BASE AND ALKYL SALICYLATE FOR THE DELIVERY OF EPHEDRINE BASE IN VAPOR FORM

BACKGROUND OF THE INVENTION

The present invention comprises a composition containing ephedrine base and an alkyl salicylate. The invention also relates to a method of delivering ephedrine base in vapor form from the composition of the invention. The invention further comprises articles of manufacture comprising the composition of the invention. The invention also further relates to the treatment of certain nasal and upper respiratory disorders by delivery of a therapeutically-effective amount of ephedrine base in a vapor form from the composition and articles of manufacture of the invention.

The common cold is usually accompanied by drainage from the nose (a "runny" nose), sneezing, cough, headache, and congestion in the nose, bronchus and lungs. One or more of these symptoms are generally relieved through systemic or topical application of an appropriate medication, such as cold tablets or capsules, cold rubs, nasal drops, nasal sprays, vapor inhalers, or others.

Ephedrine base (hereinafter also referred to simply as ephedrine) is well known to be useful in the treatment of various physiological disorders, including the symptoms of the common cold, and other disorders of the nasal mucosa and the respiratory tract. Other uses of ephedrine base include: the constriction of blood vessels; the bolstering of blood pressure of patients with spinal anesthesia; the treatment of shock; its use in the optometry field for its mydriatic effect; its use as a central nervous system (CNS) stimulant; the treatment of narcolepsy; the treatment of CNS poisoning by depressants, including barbiturates and morphine; and the treatment of myasthenia gravis.

In the treatment of these disorders, ephedrine has been used in a variety of forms and compositions. For example, sterile solutions of ephedrine have been used and administered subcutaneously, intravenously and muscularly. Solutions of ephedrine in a petroleum oil vehicle are applied topically from a level from about 1% to 3% by weight of the solution.

Ephedrine base has not been widely used in orally-administered forms such as tablets, capsules, elixirs and the like, to provide systemic delivery of the active, because it is rapidly metabolized in the body. Such an application usually utilizes a more stable active compound, particularly the salt forms of ephedrine (ephedrine sulfate or ephedrine hydrochloride), the isomer pseudoephedrine, and closely-related amine compounds such as desoxyephedrine, norephedrine, and epinephrine. As with all orally-administered actives, the onset of therapeutic activity is delayed due to the indirect delivery of the active via the digestive system through absorption into the bloodstream.

Ephedrine base is highly lipophilic and is absorbed readily through the skin and other mucosa. The transdermal adsorption of ephedrine base is several times faster than the corresponding ephedrine sulfate and hydrochloride forms. (See *Transdermal Films of Ephedrine*, Bhalla et al., Drug Development and Industrial Pharmacy, 14 (1), 119–131 (1988). Hence, ephedrine base can be a preferred compound for the treatment of disorders involving nasal mucosa and the respiratory tract if delivered directly to these areas.

There are minor problems associated with the use of ephedrine base in a product composition, including its instability in light (which can be overcome by appropriate packaging of the composition, for example, in a brown-glass bottle or sealed container), its tendency to form a more stable salt form in an aqueous solution without proper buffering, and its negligible volatility. In a petroleum oil or isotonic solution, ephedrine base exerts virtually no vapor pressure above a liquid containing as much as 10% by weight of ephedrine. Because of its poor volatility, ephedrine base has never been suggested or used in a composition or in a treatment where vapor phase delivery of the active is required. Rather, its use has been limited to direct application of the composition containing the ephedrine to a treatment site, such as the nasal cavity. Such forms are less effective and efficient since much of the active can be lost due to carrying away by natural body fluids of the mucosa, and since the liquid composition results in significant interference to effective absorption of the ephedrine by the mucosa or body tissue of the treatment site.

It would therefore be advantageous to deliver ephedrine base in the vapor phase in order to maximize absorption by the mucosa of the nasal and the upper respiratory cavity, to maximize the relative amount of surface area directly exposed to the active, and to reduce the loss of active via loss due to carrying away by natural body fluids.

SUMMARY OF THE INVENTION

A method has now been discovered for delivering ephedrine base in vapor form from a composition comprising ephedrine base and a $C_1$-$C_5$ alkyl salicylate. This composition can be formulated into a variety of articles of manufacture which can be used in various methods of treatment of disorders of the nasal mucosa and the upper respiratory tract, as well as other disorders or physiological conditions where topical or systematic delivery of ephedrine base can have a therapeutic effect.

The present invention comprises a composition comprising from about 1% to about 99%, preferably from about 2% to about 25%, most preferably from about 5% to about 10% by weight ephedrine base, and from about 1% to about 99%, preferably from about 5% to 75%, most preferably from about 10% to about 25% by weight $C_1$-$C_5$ alkyl salicylate. A preferred composition comprises the ephedrine base and the alkyl salicylate in a weight ratio from about 5:1 to about 1:20, more preferably from about 1:1 to about 1:5, most preferably from about 1:1 to 1:2.5.

A preferred composition further comprises from about 2% to about 93%, more preferably from about 25% to about 90%, most preferably from about 65% to about 85% by weight aromatic compounds. Preferred aromatic compounds include camphor, menthol, and mixtures thereof. The types and concentrations of aromatic compounds can influence the rate of ephedrine vapor release from the composition, as well as the organoleptic properties of the composition.

Articles of manufacture can also be prepared wherein the ephedrine base and the alkyl salicylate are admixed with other optional materials, either together or separately. In the case where the ephedrine base and alkyl salicylate are separately mixed with optional ingredients, the normal use of the article will result in the two materials combining together to affect the vaporization of the ephedrine. Such an article can be, for example, a throat drop or a chewy candy gum, as described hereinafter, which is placed into and dissolved in the mouth of the user.

DETAILED DESCRIPTION OF THE INVENTION

Compositions

Compositions of the present invention can be prepared by simply admixing the ephedrine base with the alkyl salicylate, and with the other optional materials including the aromatic compounds.

Ephedrine

Ephedrine is a well known naturally occurring alkaloid obtainable from a number of plant sources, such as *Ephedrine vulgaris* and *Ephedrine intermedia*, found in China and India. See for example *Choora's Indigenous Druos of India*. R. N. Chopra et al., pp. 145-147 (1933). Ephedrine base is usually found in various combinations with its pseudoephedrine isomer in these plants, at total alkaloid levels of from about 0.2% to about 2.5%. Rymill and McDonald, *Quart. J. Pharm. Pharmacol.*, 10, 463 (1937) discloses a process for extracting ephedrine from plants. The ephedrine base can be separated from pseudoephedrine and from several other well known isomers, by a variety of techniques, such as those disclosed in Paris et al., *Ann Phar. Franc*. 25, 177 (1967). Rectification of ephedrine obtained from natural resources can also remove terpenes and other organics which can interfere with the vaporization of the ephedrine from the compositions of the invention.

Ephedrine can also be synthesized, as disclosed in U.S. Pat. No. 2,509,309 (Scriabine), issued May 30, 1950; U.S. Pat. No. 1,956,950 (Hildebrandt et al), issued May 1, 1933; and U.S. Pat. No. 1,927,961 (Stolz et al), issued Sep. 26, 1933.

In its substantially pure form, ephedrine base (also identified by the chemical name α-[1-(methylamino)ethyl]benzenemethanol) is a solid, crystalline material having a melt point of about 34° C. The material is highly hygroscopic, capable of forming a hydrate of up to about 5.2% water. Formation of the hydrate raises the melting point to between about 34° C.-40° C. Ephedrine base is soluble in alcohol, chloroform, ether, and oils, and is moderately and slowly soluble in water and liquid petrolatum. Solutions of ephedrine in liquid petrolatum will become turbid, however, if the ephedrine contains more than about 1% by weight of water as a hydrate. Ephedrine base has no significant vapor pressure at ambient conditions, either in its solid form or over a solution containing the ephedrine (in the absence of the alkyl salicylate).

Alkyl Salicvlate

The $C_1$-$C_5$ alkyl salicylate of the present invention preferably comprises methyl salicylate, ethyl salicylate, amyl salicylate, and mixtures thereof. Methyl salicylate, ethyl salicylate, amyl salicylate, and mixtures thereof each affect the vaporization of the ephedrine base when combined therewith. Methyl salicylate results in a greater and more rapid vaporization of ephedrine base relative to the other alkyl salicylates. Methyl salicylate is the preferred alkyl salicylate.

Methyl salicylate is usually prepared by the esterification of salicylic acid with methanol. Commercial grade methyl salicylate is about 99% pure, and can be obtained from Aldrich Chemical Company, Inc., Milwaukee, Wis., U.S.A. Methyl salicylate is also obtainable from natural sources such as wintergreen oil (96-99% methyl salicylate).

Ethyl salicylate can be prepared by esterification of salicylic acid with ethyl alcohol and concentrated sulfuric acid in the presence of aluminum sulfate, as described by Kotake and Fujita, *Chem. Zentralbl.* 2, 454 (1928), and can be obtained in relatively pure form (99%) from Aldrich Chemical Company Inc.

Amyl salicylate can be prepared by the esterification of salicylic acid with isomeric amyl alcohol.

Minor amounts of impurities found in the natural or synthetic alkyl salicylate can effect the rate of ephedrine release and the odor profile of the compositions of the invention. If removal of these minor amounts of impurities is desired, the natural or synthetic alkyl salicylate can be rectified to reduce the level of the impurities.

Aromatic Compounds

The composition can further comprise aromatic compounds. The aromatic compounds of the present invention can be naturally occurring or synthetic, and can be used in their natural form or can be rectified to a purer form. Preferred aromatic compounds of the present invention include menthol, camphor, and mixtures thereof. Menthol and camphor are well-known articles of commerce. Other aromatic compounds include, but are not limited to, lavender oil, eucalyptus oil, pine needle oil, nutmeg oil, cedar leaf oil, cedarwood oil, turpentine, isobornyl acetate, sassafras oil, thymol and various terpenes. An exhaustive list of other aromatic compounds can be found in *The Essential Oils*. Gunther E., ed., R.E. Krieger Publishing Co., Vol. I-VI, 1976.

The type, relative amount, source, and purity of the aromatic material selected can affect the rate of ephedrine release and the odor and skin feel of the composition. For example, it has been found that thymol and terpenes are two materials which can reduce the rate of ephedrine release. One can choose to formulate without these materials, or to selectively incorporate them into the composition in order to regulate the amount or rate of ephedrine base released by the composition.

Aromatics from natural sources can contain low levels of terpenes and thymol. Menthol, which can be synthesized from thymol, can have trace amounts of unreacted thymol. If removal of terpenes and thymol is desired, the natural or synthetic aromatic compounds can be rectified to reduce their level, as well as the level of other inert organics.

The aromatic compounds are useful in formulating ointments, lotions, creams, gels, jellies, inhalants, nasal sprays, nasal drops, throat drops, oral medications and mouth washes.

Other Optional Ingredients And Actives

Other optional ingredients which can be used in the composition of the present invention include other therapeutics: decongestants, such as pseudoephedrine HCl; antitussives such as dextromethorphan; antihistamines such as chlorpheniramine maleate; analgesics such as acetaminophen; and antibacterials such as cetyl pyridinium chloride. Such therapeutics are added to the composition at a level which provide a safe and effective dosage of the respective therapeutic. The maximum safe and effective dosages for the above actives are: pseudoephedrine HCl; 60 milligrams (mg); dextromethorphan, 20 mg; chlorpheniramine maleate, 24 mg; and acetaminophen, 1000 mg. Cetyl pyridinium chloride can be used at levels up to about 0.05% by weight.

Other optional ingredients include sugars, corn syrups, plasticizers, elastomers, colorants, sweetening agents and flavorants, glycols, sorbitol, and opacifiers. These materials are useful in oral preparations such as solid, semi-solid and/or gum candy bases.

Other optional ingredients include aqueous solvents such as water, saline solutions and buffers; non-aqueous solutions such as mineral oils, silicone oils, essential oils, alcohols such as ethyl alcohol, isopropyl alcohol and mixtures thereof, used in preparation of ointments, lotions, creams, gels, jellies, inhalants, nasal sprays, nasal drops, throat drops, oral medications and mouth washes.

Other optional ingredients include petrolatum, mineral waxes, emulsifiers such as polyethylene glycol, polyethylene glycol esters, polyethylene oxide, polyethylene oxide esters, polyethylene oxide ethers, polysorbates, carbomers, cetyl alcohol and stearyl alcohol, preservatives such as methyl paraben and propyl paraben, used in the preparation of ointments, lotions, creams, gels and jellies.

Method for Delivering Ephedrine in Vapor Form

The present invention also relates to a method of delivering a therapeutically-effective amount of ephedrine base in vapor form. This method comprises the steps of forming a composition which comprises ephedrine base and alkyl salicylate, and exposing the composition to air so that the ephedrine base is vaporized from the composition into the air. By air is meant ambient atmospheric gases, but can also include any other inhalable gas. The ephedrine base can be vaporized by this method at ambient temperatures and pressures, as well as at elevated temperatures and/or pressures. The composition which can be used in this method includes the compositions described herein before. The composition can be used as-is, or can be applied to a substrate, such as a cellulosic wick or a fabric, from where the ephedrine base, alkyl salicylate, and other volatile aromatic compounds are released.

Without being bound by any particular theory, it is believed that the ephedrine base interacts either physically or chemically with the alkyl salicylate, and is vaporized along with the alkyl salicylate. The higher relative vapor pressure of methyl salicylate relative to either ethyl or amyl salicylate may account for its greater efficacy.

The delivery of ephedrine base in vapor form enables its use in various product forms to provide a method of treatment which heretofore was impossible or impractical. Delivery of ephedrine base in vapor form is particularly useful in treatments where transdermal or transmucosal absorption or adsorption is the mechanism for delivering the active.

Articles of Manufacture

The present invention also comprises various articles of manufacture which comprise the composition of the present invention. A preferred article of manufacture is a vapor inhaler such as the Vicks Inhaler TM manufactured and sold by Richardson-Vicks Inc. The vapor inhaler comprises of an enclosed cylindrically-shaped container having an orifice at one end of the cylinder and one or more vent holes in the other end. The inhaler contains a wick of cellulosic material onto which has been applied a composition of the present invention. The orifice-end of the inhaler is placed into the nasal opening. Inhaling results in air being drawn into the container through the vent holes. The air picks up vaporous ephedrine base, alkyl salicylate, and other volatiles in the composition as it passes through the container, and passes through the orifice in the end of the inhaler and into the nasal cavity and respiratory tract. The composition used in the vapor inhaler comprises ephedrine base, alkyl salicylate, preferably methyl salicylate, and preferably an aromatic compound preferably selected from the group consisting of camphor, menthol, and mixtures thereof. More preferably the composition comprised within the vapor inhaler comprises:

(a) from about 2% to about 10%, preferably from about 5% to about 10% by weight ephedrine base;

(b) from about 5% to about 75%, preferably from about 10% to about 25% by weight alkyl salicylate selected from the group consisting of methyl salicylate, ethyl salicylate, amyl salicylate, and mixtures thereof; and (c) from about 2% to about 93%, preferably from about 25% to about 90% by weight of aromatic compounds selected from the group consisting of camphor, menthol, and mixtures thereof.

Another article of manufacture comprised in the present invention consists of a composition in a viscous, semi-solid form, comprising from about 2% to about 10% by weight ephedrine base, from about 5% to about 20% by weight alkyl salicylate, from 0% to about 30% by weight aromatic compound, and from about 40% to about 93% by weight petrolatum. The article can be topically applied to the chest and throat area, or can be used in a steam vaporizer. The article can also serve as the composition comprised in the aforementioned vapor inhaler, and can be applied onto the wick, or can be contained within the inhaler as-is, replacing the wick.

Other articles of manufacture include liquid inhalant composition comprising from about 2% to about 25% by weight ephedrine base, from about 5% to about 75% by weight alkyl salicylate, from 0% to about 93% by weight aromatic compounds, and from about 0% to about 93% by weight of a liquid vehicle such as mineral oil, or a volatile liquid vehicle such as ethanol, or an essential oil or mixture of essential oils, such as sassafras oil, pine needle oil, and others. The liquid inhalant product can be dispensed onto a fabric material by the user and held on or near the nose or mouth so that the ephedrine base can vaporize from the composition and be inhaled. Alternatively, the liquid inhalant can be delivered to the nasal cavity via a mechanical device such as a spray bottle.

Another article of manufacture comprised in the present invention is a throat drop. The throat drop comprises from about 1% to about 2% by weight ephedrine base, from about 1% to about 2% by weight alkyl salicylate, from about 0% to about 5% by weight aromatic compounds, and from about 90% to about 96% by weight hard-boiled candy composition comprising one or more sugar alcohols, aromatic compounds, as well as other optional components, such as flavor oils and essences, sweeteners and others.

Similarly, cough drops can be comprised in the articles of manufacture of the present invention, by further incorporating a therapeutically safe and effective amount of an active ingredient such as an antitussive (for example, up to 20 milligrams of dextromethorphan) in the throat drop hereinbefore described.

Another article of manufacture of the present invention is a chewy candy gum, such as that described in European Patent Publication No. 0.370,296 (May 30, 1990) and incorporated hereby reference. The chewy candy gum comprises a matrix of confectionary ingredients having distributed therein multiple discrete regions of a chewing gum composition, together with multiple discrete regions of a hard-boiled candy composition. The matrix can comprise a laminate structure comprising multiple alternate layers of the chewing gum composition and the hardboilded candy composition. Alternately, the matrix can be coated with a second hardboilded candy composition which is the same as or different than the laminated hardboiled candy composition. The ephedrine base and the alkyl salicylate can be incorporated together or separately, preferably together. into either the chewy candy gum composition or into the laminated hardboilded candy composition of the chewy candy gum.

Methods of Treatment

The present invention also relates to methods of treatment of the nasal mucosa and the upper respiratory tract by administering to the person in need of such treatment a therapeutically-effective amount of the ephedrine base in vapor form. The treatment can be affected by delivering the ephedrine from a composition of the present invention via one or more of the aforementioned articles of manufacture.

The method of treatment of nasal congestion and bronchial asthma comprises administering to a person in need of such treatment ephedrine base in vapor form in an amount from about 1 microgram (mg) to about 10 mg. delivered in one to four inhalations per nostril, several times per day as needed. The preferred means for delivering the ephedrine in this treatment is a vapor inhaler.

The present invention is illustrated by the following non-limiting examples. All parts and percentages herein are by weight unless otherwise stated.

EXAMPLE I

A composition of the present invention is prepared by the following procedure:

In a suitably sized steam-jacketed stainless steel mixing vessel is added 330.8 grams menthol crystals and 330.8 grams camphor crystals. The vessel is loosely covered and the contents heated to melt the crystals while maintaining a temperature of the melted liquid of about 52° C. The menthol and camphor mixture is stirred occasionally while melting. When the crystals are completely melted, 223.8 grams methyl salicylate and 87.6 grams ephedrine base are added to the melted liquid. The menthol crystals, camphor crystals, methyl salicylate, and ephedrine base are all sourced from Aldrich Chemical Company, In., Milwaukee, Wis., U.S.A. The heat is removed and the solution is allowed to cool to ambient temperature while stirring occasionally. After the solution has cooled to ambient temperature, it is placed into a suitable brown-glass container and sealed.

The solution contains the following components by weight:

| | |
|---|---|
| Ephedrine base | 9.0% |
| Methyl salicylate | 23.0% |
| Menthol | 34.0% |
| Camphor | 34.0% |

EXAMPLE II

A method for measuring the release of ephedrine base in vapor form from the composition of Example I is as follows:

One milliliter of the solution made in Example I is drawn into a suitable glass pipet and transferred to an inhaler wick. The solution is absorbed into the wick. The wick is composed of cellulose acetate with a binder, and has dimensions of 5/16" (8 mm) diameter, ⅞" (22 mm) length, and a weight of about 0.24 grams.

The volatile materials from the solution absorbed into the inhaler wick, including ephedrine base, are caused to vaporize from the wick, are isolated using a purge and trap technique, and are analyzed by thin layer chromatography with UV detection as defined in the following analytical method.

A. General Reagents

Reference standard of Ephedrine purchased from Aldrich, Dansyl Chloride from Pierce Chemical Co., Menthol, Camphor, Thymol, Methyl Salicylate used for the aromatic base were purchased from local vendors. Hexane, Ether, Dichloromethane used were analytical grade solvents from Merck. Tenax GC, used as an absorbant in purge and trap method was purchased from Alltech Associates.

B. General Apparatus

1. Wheaton purge and trap device (Alltech Associates Cat #9051)
2. Flow manometer capable of reading minimum air flow of 10 cc/sec.
3. Glass tubes with stoppers.
4. Pierce Reactitherm Heating/Stirring module (Pierce Chemical Co. Cat #18971).
5. Reciprocal shaker mixer (laboratory fabricated).
6. Camag TLC Scanner II (Camag Sonnenmattstrasse, Switzerland) interfaced with HP 9816 computer (Hewlett Packard, Pala Alto Calif.) and HP Thinkjet printer.
7. TLC spotter: Linomat IV (Camag).
8. TLC Plates: HPTLC Silica Gel MERCK 60 F 254 10×20 cm plates (Camag Cat # 034 5642).
9. Developing Chamber: Twin rough chamber (Camag Cat #022 5254).
10. Syringe: 100 μl 1 (Camag Cat #27820).

C. TLC Conditions a. Plate conditions - Wash plates with methanol followed by conditioning at 80° C. for 1 hr.
b. Sample size - Spot 5 μl of the extract @10 sec/μl
c. No. of tracks - 13
d. Start position - 15 mm
e. Band length - 6 mm
f. Space between bands - 8 mm
g. Solvent system - Cyclohexane:Benzene:Ethyl Acetate:Isopropyl Alcohol (76:10:6:8)
h. Equilibration time - 20 min.
i. Development distance - 9 cm from spotting edge
j. Wavelength for scanning - 366 nm D. Purge and Trap Set Up 1. Preparation of cartridge Standard 1 ml size disposable pipette tips are trimmed off at a distance of 25 mm from their tapered ends to give a tube of final dimensions of 45 mm length and OD of 9 mm at the uncut end and 5 mm at the cut narrower end. The narrow end is then plugged with minimum amount of glasswool and then filled with tenax GC up to 25 mm from the narrow end. The column is then plugged with non-absorbant cotton. The narrow end of this column forms the inlet and the wider end forms the outlet for vapors.

2. Wheaton Purge and Trap Device

Wheaton Purge and Trap Device consists of a J-shaped tube connected to a larger reservoir tube by a Wheaton connector. The reservoir tube contains a sintered glass base towards the J-tube. The upper end of the reservoir tube is capped by a second Wheaton connector into which was inserted the tenax cartridge. The open end of the J-tube is connected to a regulated air source through a flow manometer and the air filter. The air flow is maintained at 22.5 cc/sec to simulate the human inhalation rate. An inhaler wick containing 1 ml of inhaler medication is transferred to the reservoir chamber. Sample is collected for period of 10 min.

E. Extractions & Derivatisation

1. After collection of the sample, transfer the tenax to a 7 ml stoppered tube.
2. Transfer 1 ml water and 100 $\mu$l 1 N HCl to acidify. Mix well. Extract with 2 ml hexane. Remove and discard hexane extract.
3. Basify with 1N NaOH to pH=9. Extract with 2×3 ml of ether: Dichloromethane (7:3). Pool both the extracts and evaporate solvent under nitrogen. Do not over dry.
4. Transfer 500 $\mu$l of Dansyl Chloride solution (200 mg Dansyl Chloride/25 ml Acetone), 200 $\mu$l of saturated $NaHCO_3$ and 100 $\mu$l of Internal standard solution (2 mg ethyl ester of phenylalanine 10 ml ethanol). Mix well and seal with teflon. Heat at 45° C. for one-half hour.
5. After derivatisation, extract the solution with 1 ml toluene. Transfer the toluene layer into another tube and evaporate under nitrogen to dryness. Reconstitute the sample in 75 $\mu$l toluene.

Calculations

1. The amount of ephedrine trapped is determined from a calibration plot of peak areas versus known amounts of ephedrine. For calibration, prepare a standard solution of ephedrine in methanol (5 mg/10 ml) and spike 0.2, 0.4, 0.6 and 0.8 Bml onto the tenax trap to deliver 10, 20, 30 and 40 $\mu$l, resp., of ephedrine. Extract and derivatize as per section (D).
2. Calibration curves are constructed by plotting the ratios of peak area to internal standard versus amount spike ($\mu$g). Subject the curve to linear regression analysis and fit straight line of the equation $Y=mX+c$. The sample amount (in $\mu$g) is read from the calibration curve.
3. The values thus obtained represent amounts of ephedrine released in 10 min. Thus, the rate of ephedrine release (ng/sec) can be calculated from:

$$\frac{ng}{sec} = \frac{amt.\ released\ (\mu g)}{10\ min} \times \frac{10\ min}{600\ sec} \times \frac{1000\ ng}{\mu g}$$

EXAMPLE III

A vapor inhaler for use in the treatment of nasal congestion is made as follows:

An inhaler wick as described in Example II, without medication, is placed into the bottom opening of an inhaler tube. The inhaler tube is cylindrically shaped, having a length of 2.44" (62 mm) and a bottom opening diameter of 0.44" (11.2 mm) bottom opening, and weighs about 1.98 grams. The inhaler tube has threads on the outside on the bottom end to accept an inhaler cover. The inhaler tube has four approximately 1.5 mm diameter vent holes along the bottom, and an approximately 3 mm inhalation opening in the top end. The vent holes allow for air to be drawn into the inhaler tube, along the length of the inhaler tube and the inhaler wick, and out the inhalation hole. An inhaler plug is press-fitted into the bottom opening of the inhaler tube, thereby enclosing the inhaler wick inside the inhaler tube. The inhaler tube and the inhaler plug are made of polypropylene, for example Eastman 4240-G or Amoco 4018.

One milliliter of the solution of Example I is drawn into a suitable glass pipet and is applied to the inhaler wick through the inhalation opening at the top end. An inhaler cover (cylindrical shape, 2.28" (58 mm) in length and 2.9 grams weight), having internal threads to mate with the inhaler tube, is screwed onto the inhaler tube. The inhaler cover is made of polypropylene, for example Amoco 4916 or 4918, or Hercules Profax 6231.

EXAMPLE IV

The treatment of nasal congestion by delivery of volatile ephedrine base is achieved by using the vapor inhaler of Example III in the following manner:

After removing the inhaler cover, the top end of the vapor inhaler tube is placed in one nostril. While covering the other nostril, the user takes four deep inhalations. The procedure is repeated in the other nostril. The amount of ephedrine base delivered in each nostril is approximately therapeutically equivalent to two drops of a conventional nasal decongestant solution containing 0.65% (w/w) ephedrine HCl solution.

What is claimed is:

1. A method of treatment of disorders of the nasal mucosa and the upper respiratory tract by administering to a human or animal in need of the treatment a therapeutically-effective amount of ephedrine base in vapor form released from a composition comprising from about 1% to about 99% by weight ephedrine base and from about 1% to about 99% by weight $C_1$-$C_5$ alkyl salicylate.

2. A method of treatment according to claim 1 for nasal congestion and the relief of bronchial asthma.

3. A method of treatment according to claim 2 wherein the ephedrine base in vapor form is nasally or orally inhaled and is released in vapor form from a composition comprising:
   (1) from about 2% to about 25% by weight ephedrine base, and
   (2) from about 5% to about 75% by weight alkyl salicylate selected from the group consisting of methyl salicylate, ethyl salicylate, amyl salicylate, and mixtures thereof.

4. A method of treatment according to claim 3 comprising from about 5% to about 10% ephedrine base and from about 10% to about 25% alkyl salicylate.

5. A method of treatment according to claim 4 wherein the composition further comprises from about 2% to about 93% by weight aromatic compound.

6. A method of treatment according to claim 4 or 5 wherein the amount of ephedrine base delivered by the treatment is from about 1 microgram to about 10 micrograms, delivered in from one to four inhalations per nostril, several times per day as needed.

7. A method of treatment according to claim 3 wherein the weight ratio of ephedrine base to alkyl salicylate is from about 5 to 1 about 1 to 20.

8. A method of treatment according to claim 3 wherein the alkyl salicylate is methyl salicylate.

9. A composition for use in delivering ephedrine base in vapor form for administration to a human, comprising:
   (1) from about 1% to about 99% by weight ephedrine base, and
   (2) from about 1% to about 99% by weight $C_1$-$C_5$ alkyl salicylate.

10. A composition according to claim 9 comprising:
    (1) from about 2% to about 25% by weight ephedrine base, and
    (2) from about 5% to about 75% by weight alkyl salicylate.

11. A composition according to claim 10 comprising:
    (1) from about 5% to about 10% by weight ephedrine base, and
    (2) from about 10% to about 25% by weight lkyl salicylate.

12. A composition according to claim 9, 10, or 11 wherein the alkyl salicylate is selected from the group consisting of methyl salicylate, ethyl salicylate, amyl salicylate, and mixtures thereof.

13. A composition according to claim 12 wherein the alkyl salicylate is methyl salicylate.

14. A composition according to claim 12 wherein the weight ratio of (1):(2) is about 5:1 to about 1:20.

15. A composition according to claim 14 wherein the weight ratio of (1):(2) is about 1:1 to about 1:5.

16. A composition according to claim 9, 10, or 11 further comprising from about 2% to about 93% by weight aromatic compound.

17. A composition according to claim 13 comprising from about 25% to about 85% aromatic compound.

18. A composition according to claim 17 wherein the aromatic compound is selected from the group consisting of camphor, menthol, sassafras oil, pine needle oil, eucalyptus oil, and mixtures thereof.

19. A composition in the form of a viscous semi-solid for use in delivering ephedrine base in vapor form comprising:
    (1) from about 2% to about 10% by weight ephedrine base;
    (2) from about 5% to about 20% by weight alkyl salicylate selected from the group consisting of methyl salicylate, ethyl salicylate, amyl salicylate, and mixtures thereof;
    (3) from 0% to about 30% by weight aromatic compound; and
    (4) from about 40% to about 93% by weight petrolatum.

20. A composition for use in delivering ephedrine base in vapor form comprising:
    (1) from about 2% to about 25% by weight ephedrine base;
    (2) from about 5% to about 75% by weight $C_1$-$C_5$ alkyl salicylate selected from the group consisting of methyl salicylate, ethyl salicylate, amyl salicylate, and mixtures thereof;
    (3) from 0% to about 93% by weight aromatic compound; and
    (4) from 0% to about 93% by weight of liquid vehicle selected from the group consisting of:
      (i) mineral oil;
      (ii) ethanol, isopropyl alcohol, and a mixture thereof;
      (iii) essential oil; and
      (iv) mixtures thereof.

21. A composition for use in delivering ephedrine base in vapor form comprising:
    (1) from about 1% to about 2% by weight ephedrine base;
    (2) from about 1% to about 2% by weight alkyl salicylate selected from the group consisting of methyl salicylate, ethyl salicylate, amyl salicylate, and mixtures thereof;
    (3) from 0% to about 5% by weight aromatic compound; and
    (4) from about 90% to about 96% by weight hard-boiled candy composition.

* * * * *